US006361815B1

(12) United States Patent
Zheng et al.

(10) Patent No.: US 6,361,815 B1
(45) Date of Patent: Mar. 26, 2002

(54) PRODUCTS COMPRISING TRIHYDROXYSTILBENES AND DERIVATIVES THEREOF AND METHODS FOR THEIR MANUFACTURE AND USE

(75) Inventors: Bo Lin Zheng, Wayne; Calvin Hyungchan Kim, Fort Lee; Kan He, River Edge; Qun Yi Zheng, Wayne, all of NJ (US)

(73) Assignee: Pure World Botanicals, Inc., South Hackensack, NJ (US)

( * ) Notice: Subject to any disclaimer, the term of this patent is extended or adjusted under 35 U.S.C. 154(b) by 0 days.

(21) Appl. No.: 09/217,642

(22) Filed: Dec. 21, 1998

(51) Int. Cl.$^7$ ............................................... A61K 31/05
(52) U.S. Cl. ...................... 426/489; 426/425; 426/429; 426/478; 514/733; 514/736
(58) Field of Search .................. 514/733, 736; 426/425, 429, 478, 489

(56) References Cited

U.S. PATENT DOCUMENTS 5,747,536 A * 5/1998 Cavazza ...................... 514/556
6,238,673 B1 * 5/2001 Howard ................... 424/195.1

FOREIGN PATENT DOCUMENTS

| JP | 60-9455 | 1/1985 |
| JP | 609455 | * 1/1985 |

OTHER PUBLICATIONS

Waterhouse et al., Phytochemistry, vol. 37(2), pp. 571–573, 1994.*
Kimura et al., Journal of Medicinal Plant Research, vol. 49, pp. 51–54 (1983), Effects of Stilbene Components of Roots of Polygonum ssp. on Liver Injury in Peroxidized Oil–fed Rats.
Raventos et al., J. Agric. Food Chem., 43, pp. 281–283 (1995), Direct HPLC Analysis of cis– and trans–Resveratrol and Piceid Isomers in Spanish Red Vitis vinifera Wines.
Raventos et al., J. Agric. Food Chem., vol. 41, No. 4, pp. 521–523 (1993), Occurence of Resveratrol in Selected California Wines by a New HPLC Method.
Jeandet et al., J. Agric. Food Chem., vol. 43, pp. 316–319, (1995) Effect of Enological Practices on the Resveratrol Isomer Content of Wine.
Orsini et al., J. Nat. Prod., vol. 60, pp. 1082–1087 (1997), Isolation, Synthesis and Antiplatelet Aggregation Activity of Resveratrol 3–O–β–D–Glucopyranoside and Related Compounds.
Jayatilake et al., Journal of Natural Products, vol. 56, No. 10, pp. 1805–1810 (1993), Kinase Inhibitors from Polygonum Cuspidatum.
Chung et al., Planta Med., vol. 58, pp. 274–276 (1992), An Antiplatelet Principle of Veratrum formosanum.

Sharma et al., Cancer Research, vol. 54, pp. 5848–5855 (1994), Screening of Potential Chemopreventive Agents Using Biochemical Markers of Carcinogenesis.
Goldberg et al., Anal. Chem., vol. 66, pp. 3959–3963 (1994), Direct Injection Gas Chromatographic Mass Spectrometric Assay for trans–Reseveratrol.
Kimura et al., Biochem. et Biophys. Acta, vol. 834, 275 (1985), Effects of stilbenes on arachidonate metabolism in leukocytes.
Jang et al., Science, vol. 275, pp. 218–220 (1997), Cancer Chemopreventive Activity of Resveratrol, a Natural Product Derived from Grapes.
Pettit et al., Can. J. Chem., pp. 1374–1376 (1982), Isolation and structure of combretastatin.
Pezet et al., Journal of Chromatography A, vol. 663, pp. 191–197 (1994), Method to determine resveratrol and pterostilbene in grape berries and wines using high–performance liquid chromatography and highly sensitive fluorimetric detection.
Arichi et al. Chem. Pharm. Bull., vol. 30, pp. 1766–1770 (1982), Effects of Stilbene Components of the Roots of Polygonum cuspidatum SIEB. et Zucc. on Lipid Metabolism.
Gonzalez et al., Phytochemistry, vol. 32, No. 2, pp. 433–438 (1993), Stilbenes and Other Constituents of Knema Austrosiamensis.
Rowe et al., Phytochemistry, vol. 8, pp. 235–241 (1969), Extractives of Jack Pine Bark: Occurrence of CIS– and Trans–Pinosylvin Dimethyl ether and Ferulic Acid Esters.
Mannila et al., Phytochem, vol. 33, pp. 813–816 (1992), Anti–Leukaemic Compounds Derived from Stilbenes in picea Abies Bark.
Waterhouse and Raventos, Phytochemistry, vol. 37, No. 2, pp. 571–573 (1994), The Occurrence of Piceid, A Stilbene Glucoside, in Grape Berries.
Langcake et al., Physiological Plant Pathology, vol. 9, pp. 77–86 (1976), The production of resveratrol by Vitis vinifera and other members of the Vitaceae as a response to infection or injury.
Shan et al., Acta Pharmacologica Sinica, vol. 11, pp. 527–530 (1990), Influences of 3,4,5–trihydroxystibene–3–β–mono–D–glucoside on rabbits platelet aggregation and thromboxane $B_2$ production in vitro.

(List continued on next page.)

*Primary Examiner*—James O. Wilson
*Assistant Examiner*—Howard V. Owens, Jr.
(74) *Attorney, Agent, or Firm*—Dechert

(57) ABSTRACT

Provided are products including trihydroxystilbenes and glycosylated derivatives thereof. Also provided are compositions containing these products with an aqueous solvent, particularly and alcohol-water mixture, and reverse phase chromatographic methods for isolating and purifying the compositions from plant materials. The products have biological activity, including anti-tumor activity.

18 Claims, No Drawings

OTHER PUBLICATIONS

Jeandet et al., Am. J. Enol. Vitic., vol. 46, No. 1, pp. 1–4 (1995), Resveratrol Content of Wines of Different Ages: Relationship with Fungal Disease Pressure in the Vineyard.

Kantz and Singleton, Am. J. Enol. Vitic., vol. 41, No. 3, pp. 223–228 (1990), Isolation and Determination of Polymeric Polyphenols Using Sephadex LH–20 and Analysis of Grape Tissue Extracts.

Jeandet et al., Am. J. Enol. Vitic., vol. 42, No. 1, pp. 41–46 (1991), The Production of Resveratrol (3,5,4'–trihydroxstilbene) by Grape Berries in Different Developmental Stages.

Creasy and Coffee, J. Amer. Soc. Hort. Sci, vol. 113(2), pp. 230–234 (1988), Phytoalexin Production Potential of Grape Berries.

Jeandet et al., Journal of Wine Research, vol., 3, No. 1, pp. 47–57 (1992), The Production of Resveratrol(3,5,4'–Trihydroxystilbene) by Grapevine in vitro Cultures and its Application to Screening for Grey Mould Resistance.

Jang et al., Costmetics & Toiletries, vol. 112, No. 3, pp. 59–62 (1997), Melanogenesis Inhibitor from Paper Mulberry.

* cited by examiner

PRODUCTS COMPRISING TRIHYDROXYSTILBENES AND DERIVATIVES THEREOF AND METHODS FOR THEIR MANUFACTURE AND USE

The present invention relates to trihydroxystilbenes and the glycosylated derivatives thereof. The present invention also relates to methods for isolation and purification of these products using reverse phase liquid chromatography and a method for converting glycosylated to aglycone product. The present invention further relates to treatment of diseases using compounds of the invention.

Resveratrol, 3,4',5-trihydroxystilbene, was first isolated from grape leaves (Inghim, T. L., *Phytochem.*, 15 (1979) (1976)). Inghim characterized the structure of resveratrol using chemical methods. Resveratrol has following chemical structure in which both $R_1$ and $R_2$ are hydrogen.

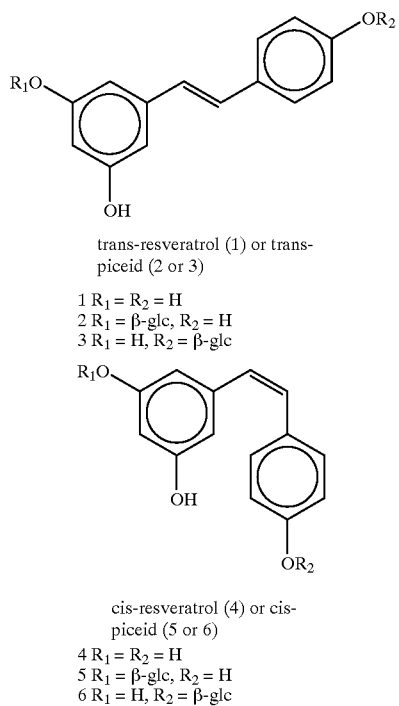

trans-resveratrol (1) or trans-piceid (2 or 3)

1 $R_1 = R_2 = H$
2 $R_1 = \beta$-glc, $R_2 = H$
3 $R_1 = H, R_2 = \beta$-glc cis-resveratrol (4) or cis-piceid (5 or 6)

4 $R_1 = R_2 = H$
5 $R_1 = \beta$-glc, $R_2 = H$
6 $R_1 = H, R_2 = \beta$-glc

Where $\beta$-glc is $O$-$\beta$-D-glucose

Trihydroxystilbenes and derivatives thereof derivatives are reported to have medicinal properties including anti-leukemic and anti-tumor activities. For example, plant material containing resveratrol has been used as an herbal medication for treatment of hyperlupemia and liver diseases in China and Japan for many centuries (Kimura, K. M. et al., *Shoygakugaku Zasshi*, 83, 35–58 (1981)). Subsequent experiments with purified trans-resveratrol demonstrate that the many biologically useful functions, including modulation of hepatic cholesterol synthesis, inhibition of lypooxygenase activity (Kimura, Y. et al., *Biochem. Biophys. Acta.* 834, 275 (1985)), inhibition of anaphylactoid (Ragazy, E., et al., *Pharmacol. Ref. Commun.*, 79, 20 (1988)), and protection of lypoproteins against oxydative and free radical damage (Frankel, E. N., et al. *Lancet*, 1, 1017 (1979)).

Recent literature reports indicate that the extract derived from *Cassia quinquangulata Rich* (*neguminasae*) collected in Peru is a potent inhibitor of cyclooxygenase (COX) (Kudo, T. et al., *Gann*, 71, 260 (1980), Pollard, M. et al., *Cancer Lett.*, 21, (1983), Waddell, W. R. et al., *Am. J. Surg.*, 157, 175 (1989), Thun, M. J. et al., *N. Engl. J.Med.*, 325, 1593 (1991)).

In the following discussion, $ED_{50}$ represents effective dosage for 50% inhibition.

In a recent article, Meishiang Jang reported that resveratrol inhibits the hydroperoxidase activity of COX-1, $ED_{50}=3.7\,\mu M$, and also hydroperoxidase activity of COX-2, $ED_{50}$-85 $\mu M$ (Jang, M. et al., *Science*, 275 218 (1997). This inhibitory activity is relevant to cancer therapy and prevention because COX catalyzes the conversion of arachidonic acid to pro-inflammatory substances such as prostaglandins, which can stimulate tumor cell growth and suppress immune responses (Plescia, O. J. et al., *Proc. Nat. Acad. Sci. USA.*, 72, (1975)).

3,4'5-Trihydroxystilbene (Resveratrol) has also been found to inhibit certain events associated with tumor growth. For instance, resveratrol inhibits the free radical formation, $ED_{50}=27\,\mu M$, when human promyclocytic leukemia cells were treated with 12-O-tetradecanoylphorbol-13-acetate (TPA) (Shama, S. et al. *Cancer Res.* 54 5848 (1994). Moreover, Jang et al. investigated the anti-inflammatory activity of resveratrol. In the carrageenan-induced model of inflammation in rats, resveratrol significantly reduced pedal edema both in the acute phase (3 to 24 hours) and the chronic phase (24 to 144 hours). The edema-suppressing activity of resveratrol was greater than that of phenylbutazone and similar to that of indomethacin. Jang et al. also investigated the effect of resveratrol in a mouse mammary gland culture model of carcinogenesis. Resveratrol, in a dose-dependent manner, inhibited the development of DMBA-induced preneoplastic lesions ($ED_{50}=3.1\,\mu M$). (Jang, M. et al., *Science*, 275, 218 (1997)).

There has recently been an increase in interest in resveratrol and analogous compounds as a result of epidemiological data showing a lower incidence of mortality due to cardiovascular damage in populations with a high-calorie high-lipid diet, but whose diet also includes red wine, as compared to populations who had a lower calorie consumption and lower percentage of lipids, but whose diet does not include red wine (Seigneur, M. et al. *J. Appl. Card.*, 5, 215 (1990); Siemann, E. H. and Creasy, L. L., *Am. J Enol. Vitic.* 43, 49 (1992); Renaud, S. and De Lorgeril, M., *Lancet*, 339, 1523 (1992); Scharp, D., Lancet. 341 27 (1993)).

Investigations have revealed that resveratrol effectively possesses many pharmacological activities which can potentially explain the protective effects of red wine at the cardiovascular level (Frankel, E. N. et al., *Lancet*, 341 454 (1993)). In addition, resveratrol has proved capable of promoting the formation of nitroxides which have a vasodilatory action and inhibit platelet aggregation induced by collagen or ADP (Fitzpatrick, D. et al., *Am. J Physiol.*, 265 (*Heart Circ. Physiol.*), 34 774 (1993)).

Plant materials that are natural sources for resveratrols include *Vitis vinifera* and *Polygonum cuspidatum* (Huzhang). The concentration of resveratrol in *P. cuspidatum* is much higher than in *V. vinifera*. The procedures currently practiced for isolating resveratrols from plant materials are very difficult and low yielding normal phase chromatographic procedures that also use chlorinated solvents which are toxic to humans and can damage the environment.

The isolation of resveratrols from natural sources represents a potential reliable source of supply. The present invention provides an isolation and purification technique which provides high yields and low cost of production of resveratrol and related compounds.

SUMMARY OF THE INVENTION

By the present invention, products containing a stilbene fraction, compositions containing these products, and reverse phase liquid chromatography processes for isolating and purifying these products from plant material are identified.

The present invention provides a first product having a solids content of at least about 60% wherein the solids include at least about 10% by weight of a stilbene fraction and a process for making the product that includes the step of contacting a plant material with an alcohol and obtaining the product from the alcohol after contacting.

Also provided is a second product obtained by mixing the first product with a pharmaceutically acceptable processing excipient and drying the resulting mixture.

The present invention further provides a third product made up of at least about 20% by weight of a mixture of trihydroxystilbenes and mono-β-D-glycosylated trihydroxystilbenes and a composition of the third product with an aqueous solvent. According to the present invention, the composition including the third product is made by an MD-1 reverse phase liquid chromatography process.

Similarly, the present invention provides fourth products made up of at least about 30% by weight of a stilbene fraction including trihydroxystilbenes and mono-β-D-glycosylated trihydroxystilbenes and compositions of these fourth products with aqueous solvents. Fourth products are made using an MD-2 process starting with a composition containing the third product in which a polyamide resin is the stationary phase. A composition containing the third product is concentrated to form a loading concentrate that is loaded onto an MD-2 column, optionally using a washing elution volume, followed by elution with one or more MD-2 elution volumes of an aqueous solvent, especially a mixture of an alcohol and water to make an MD-2 effluent that is a composition containing a fourth product. The effluent is collected in toto or as gradient fractions collected by fractionate collection. Fourth products are obtained by removing aqueous solvent from an MD-2 effluent, however collected.

The present invention also provides fifth products that are made up of at least about 60% of a stilbene fraction. A fifth product can be at least about 85% by weight mono-β-D-glycosylated trihydroxystilbenes or at least about 85% aglycone thereof. Also provided are compositions including fifth products and an aqueous solvent. Fifth products are made by an MD-3 process in which the stationary phase is silica gel based. The starting material for an MD-3 process is an effluent, especially a gradient fraction, from an MD-2 process. The effluent is concentrated to form a loading concentrate that is eluted through the MD-3 column and can be followed by a washing elution volume. The MD-3 column is then eluted with one or more elution volumes of an aqueous solvent. Each elution volume can consist of one or more discrete gradient volumes, each made up of a different aqueous solvent, or the composition of each elution volume can vary linearly, exponentially, logarithymically, hyperbolically, or stepwise during elution of the elution volume. The effluent from a first MD-3 process is a composition containing a fifth product. The effluent may be collected in toto or fractionate collected as gradient fractions. Fifth products are obtained by removing aqueous solvent from effluent or gradient fractions of a first MD-3 process. A gradient fraction of a first MD-3 process is the starting material for a cold crystallization process to make a fifth product that contains at least about 85% by weight mono-β-D-glycosylated trihydroxystilbene. The gradient fraction of a first MD-3 process is concentrated to a solids content of at least about 20 g/L and then diluted with water. The resulting mixture is cooled to less than about 0° C. to form a slurry from which such fifth product can be isolated, washed, and then dried.

Similarly, the present invention provides a second MD-3 process for making compositions containing sixth products that are at least about 70% by weight, trihydroxystilbenes. Sixth products are isolated by removing aqueous solvent from the compositions. Starting material for a second MD-3 process is an MD-2 gradient fraction that has been fractionate collected. The MD-2 gradient fraction is concentrated to a loading concentrate having a solids content of at least about 7 g/L. The MD-3 column is eluted with first and second MD-3 elution volumes that are made up of aqueous solvent. Either or both MD-3 elution volumes can be made up of gradient volumes that include different aqueous solvents or the composition of the aqueous solvent of either or both elution volumes may be varied linearly, exponentially, logarithymically, hyperbolically, or stepwise during elution of the respective elution volume. Effluents corresponding to the respective elution volumes or gradient volumes can be collected in toto or fractionate collected. Sixth products are obtained by removing aqueous solvent from the effluent or gradient fractions of a second MD-3 process, however collected.

An effluent or gradient fraction of a second MD-3 process is a starting material for making a sixth product that is at least about 85% by weight, 3,4',5-trihydroxy-trans-stilbene in which the effluent or gradient fraction is concentrated to a concentrated composition and twice contacting this concentrated composition with separate extraction volumes of a volatile polar organic solvent (e.g., ethyl acetate), combining the extraction volumes, and removing the volatile polar organic solvent to obtain the 85% product. An alternative process for making the 85% product is provided in which an elution volume or gradient fraction from a second MD-3 process is evaporated to dryness, the residue so formed dissolved in water at a temperature greater than 0° C. to form a solution, the solution cooled to less than about 0° C. to form crystals, and separating the crystals from supernatant to obtain the 85% sixth product.

The present invention also provides a third MD-3 process for making a composition containing a seventh product that includes at least 50% by weight of 3,4',5-trihydroxy-cis-stilbene. Starting material for a third MD-3 process is a fractionate collected gradient fraction of a second MD-2 process. The fractionate collected gradient fraction of a second MD-2 process is concentrated to a solids content of at least about 7 g/L to form a loading concentrate that is eluted through an MD-3 column. The third MD-3 process further includes the steps of eluting the MD-3 column with first, second, and third elution volumes that are made up of aqueous solvent. Each of the elution volumes can be made up of two or more gradient volumes in which the aqueous solvent has the same or a different composition. The elution volumes or gradient volumes result in MD-3 effluents of a third MD-3 process. The elution volumes or gradient volumes are collected to toto or fractionate collected. The effluents of the third MD-3 elution volume of a third MD-3 process, or gradient fractions thereof, are compositions containing the seventh product of the present invention. The seventh products of the present invention are obtained by removing aqueous solvent from the effluent resulting from the third MD-3 elution volume of a third MD-3 process, or gradient fractions thereof.

A process for converting a mono-β-D-glycosylated trihydroxystilbene to the corresponding aglycone is also provided. The process includes the steps of providing a solution or suspension of a glycosolated trihydroxystilbene, contacting the solution or suspension with HCl at a total concentration between 0.01 and 0.02 g/ml, and refluxing the acidified solution or suspension for about 10 to about 200 minutes. The corresponding aglycone is isolated from the reaction mixture by techniques as are known in the art. The converting process can be carried out under a blanket of inert gas, for example, nitrogen.

Definitions

Alcohol. As used herein, the term alcohol refers to a lower aliphatic alcohol, in particular one selected from the group consisting of methanol, ethanol, the isomeric propanols, the isomeric butanols, the isomeric pentanols, and the isomeric hexanols.

Aqueous Solvent. As used herein, the term aqueous solvent refers to water or a polar organic solvent that is miscible with water in all proportions from 1:99 to 99:1. Examples of polar organic solvents that are, or can be used, as components of an aqueous solvent, as that term is herein used, includes but is not limited to methanol, ethanol, isopropanol, n-propanol, acetone, and acetonitrile. Other suitable polar organic solvents are known to the skilled artesian.

Column Volume. As used herein, column volume refers to the volume of the space defined by the inner surface of the chromatography column or chamber that surrounds the RPLC stationary phase. Column volume is abbreviated herein as CV.

Composition. As used herein, the term composition is a slurry, suspension, dispersion, or especially a solution of a material, normally solid at room temperature, in an aqueous solvent. Examples of compositions include but are not limited to loading elutions, loading concentrates, and effluents or gradient fractions from any reverse phase liquid chromatography process of the present invention.

Fractionate Collecting. When used in connection with an effluent or a gradient effluent, or a gradient fraction, the term fractionate collecting denotes that the effluent or gradient effluent or gradient fraction or gradient subfraction is segregated into at least two portions or aliquots.

MD-1 Column. An MD-1 column is a reverse phase liquid chromatography column of any size in which the stationary phase is a crosslinked copolymer of a vinyl aromatic compound, for example styrene, cross linked with a polyvinyl aromatic compound, for example divinylbenzene, wherein the stationary phase has a mean surface area of at least about a 400 $m^2$/g, preferably 800 $m^2$/g, and a porosity of at least about 0.55 ml/ml, preferably at least 0.58 ml/ml. The mean diameter of the particles comprising the stationary phase is between about 490$\mu$ and 700$\mu$. The dipole moment of the crosslinked polymer comprising the stationary phase is less than about 0.5. Water is used for conditioning an MD-1 column.

MD-2 Column. An MD-2 column is a reverse phase liquid chromatography column of any size in which the stationary phase is a polyamide resin. As used herein, polyamide resin is a polymer of a lactam or a copolymer of a diamine and a dicarboxylic acid (or of the salt formed between the diacid and the diamine). Examples of polyamide resins include poly(caprolactam) and poly(hexamethylene adipamide). An alcohol water mixture comprising 10 vol-% methanol is used to condition an MD-2 column.

MD-3 Column. An MD-3 column is a reverse phase liquid chromatography column of any size in which the stationary phase is silica gel based reverse phase particles having $C_8$ to $C_{18}$, alkane moieties or cyano moieties bonded to its surface. A suitable material is WP Octadecyl reverse phase media available from J. T. Baker, Phillipsburg, N.J. (Cat. #7248-2).

An MD-3 column is conditioned with a mixture of methanol and water comprising about 20 vol-% methanol.

Percent Solid. As used herein, the quantity percent solids refers to the weight of a nominally solid composition comprising an aqueous solvent that remains after the aqueous solvent is removed. Unless otherwise indicated, the quantity percent solid is expressed as the ratio of the weight of the composition remaining after removal of aqueous solvent divided by the weight of the composition before removal of the aqueous solvent, multiplied by 100. A nominally solid composition is a composition that does not flow under its own weight at room temperature.

Pharmaceutically acceptable processing excipients. Pharmaceutically acceptable processing excipients are pharmaceutically acceptable organic or inorganic carrier substances that do not react or otherwise interfere with biologically active components of pharmaceuticals or neutriceuticals and which assist in processing the biologically active components, or products containing them, into a form convenient for administering the biologically active components to an animal, including a human. Many such pharmaceutically acceptable processing excipients are known in the art. Among these, tricalcium phosphate and maltodextrin are particularly preferred.

SDA. As used herein SDA refers to specially denatured alcohol. See U.S. Pharmacopoeia.

Solids Component. The portion of a slurry, suspension, dispersion or solution is an aqueous solvent that remains after the aqueous solvent is removed. Synonymous with solids portion.

Solids Content. As used herein, the term solids content quantifies the portion of a solution, slurry, suspension, or dispersion in an aqueous solvent that remains when the aqueous solvent is removed and is expressed in units of grams of solid remaining per liter of solution or slurry and is abbreviated g/L.

Stilbene Fraction. Stilbene fraction refers collectively to the constituents or components of a material especially a solids component, that consists essentially of 1,2-diphenylethenes and substituted 1,2-diphenylethenes, where either or both of the phenyl rings can bear one or more substituents.

Volume Percent. As used herein the term volume percent, abbreviated vol-%/, is used to describe the composition of an aqueous solvent. The vol-% of a component represents the ratio of the volume of the component added to a composition to the total of the volumes of all components added to the composition times 100. The volume percent of an aqueous solvent can be easily calculated at the time it is formulated or it can be determined later using standard techniques, for example, GL chromatography using suitable reference mixtures.

In one embodiment, the present invention provides a first product that comprises at least about 60%, preferably at least about 65%, by weight solids which solids comprise at least about 10%, preferably at least about 12%, by weight of a stilbene fraction. According to the present invention, the first product can be obtained by providing a solid plant material, preferably *V. vinifera,* more preferably *P. cuspidatum,* which plant material has been cut or ground to pieces having an average volume from about 0.001 $mm^3$ to about 15 $mm^3$, and contacting the plant material with an aqueous solvent, preferably an alcohol-water mixture comprising about 75 volume percent (vol-%) SDA. The contacting may be by any suitable means as are known in the art; for example, percolation, vat extraction, counter current extraction, and the like. The first product can then be obtained by removing aqueous solvent or a component thereof from the resulting composition. In this or any embodiment, aqueous solvent can be removed by any of the means as are known in the art such as evaporation, distillation, and lyophilization, to mention a few.

The first product can be used to prepare a second product that can be directly administered to an animal, including a human, and which second product has a stilbene fraction amounting to at least about 8% by weight and at least one pharmaceutically acceptable processing excipient.

According to one embodiment of the present invention, the second product is made by slurrying the first product in water and homogenizing the slurry with one or more pharmaceutically acceptable processing excipients. A Silverson Model 14 RT-A homogenizer, Silverson Corporation, East Longmeadow, Mass. is suitable for this purpose. The homogenized mixture is then dried by spray drying or vacuum drying.

According to another embodiment of the invention, the first product is also useful as a starting material for preparation of products having a stilbene fraction of at least about 20% by weight or for the preparation of trihydroxystilbenes and glycosylated derivatives thereof by employing reverse phase liquid chromatography processes.

In reverse phase liquid chromatography (RPLC) as practiced in embodiments of the present invention, the column packing (stationary phase, or adsorbent) is non-polar, typically having a dipole moment of 3 or less. Silica gel that has been treated to provide it with a bonded surface layer that is paraffinic in nature is an example of a stationary phase for reverse phase chromatography. Silica gels having permanently bonded $C_8$ to $C_{18}$ alkyl groups are commercially available as a stationary phase. Reverse phase liquid chromatography columns are eluted with eluents of decreasing polarity which causes the more polar compounds loaded on a column to elute first.

Reverse phase liquid chromatography stationary phases of organic material are also known. Polymers of vinyl aromatic compounds, for example styrene, that are heavily crosslinked with polyvinylic aromatic hydrocarbons, for example divinylbenzene, can be used as stationary phases for reverse phase liquid chromatography. These organic polymeric stationary phases are made by processes that yield small, extremely rigid, macroreticular particles. Highly crosslinked acrylic polymers are also useful as stationary phases for reverse phase liquid chromatography. Suitable stationary organic phases are commercially available. For example, styrenic and acrylic stationary phases are available from the Rohm and Haas Company, Philadelphia, Pa., under the trade name Amberlite®. Styreneic stationary phases are also available under the trade name Amberchrom® from Tossohass, Montgomeryville, Pa. Polyamide resins (e.g. nylons), polyester resins, and phenolic resins are also useful stationary phases for the reverse phase chromatography processes of the present invention.

Many polar organic solvents are suitable eluents for reverse phase liquid chromatography. Lower alcohols, such as methanol, ethanol, and propanol, as well as nitrites such as acetonitrile, are used as organic eluents. Lower aliphatic ketones such as acetone, methyl ethyl ketone, and diethyl ketone, as well as cyclic ethers such as tetrahydrofuran, can also be used. Dimethyl formamide, dimethyl sulfoxide, and alkyl esters of acetic acid such as ethyl acetate can also be used. Mixtures of such solvents in various proportions can be used when it is desired to elute or wash the column with solvents of varying polarity, from high to low relative polarity. Applicants have found that mixtures of water and an alcohol, for example, methanol, ethanol, n-propanol, iso-propanol, n-butanol, and n-and sec-hexanol, are particularly useful as mobile phases or eluents for separating and purifying stilbene compounds, especially those obtained from plant material. The RPLC processes of the present invention are advantageously carried out using an eluent of variable composition, that is a so-called gradient eluent. The limits of concentration of gradient eluents are determined by the concentration of polar organic solvent necessary to elute products from the stationary phase and by the requirement that the polar organic solvent be miscible to form a single phase at the required concentration.

In certain embodiments of the present invention the initial alcohol concentration is 10 volume percent (10 vol-%) or less and is increased as separation and purification proceeds.

The reverse phase liquid chromatography systems used to practice the present invention may be either preparative or analytical. Preparative columns require larger loading capacity and are typically larger in size.

Flow rates of the eluent are adjusted according to the column dimensions, the degree of separation desired, the particle size of the stationary phase, and the back pressure in the column. The separation is typically carried out at 20° C. to 30° C. However, a temperature up to about 45° C. can be used. The separation may be carried out at high pressure (500–200 psi) or moderate pressures (100–500 psi) or, preferably, at lower pressures (10–100 psi).

With regards to the dimensions of the reverse phase liquid chromatographic column, the loading of the column, the temperature, and flow rate, one skilled in the art will know to vary these parameters based primarily upon practical considerations known in the art.

The product to be chromatographically treated is generally provided as a solution or suspension in an aqueous solvent. Preferably, the aqueous solvent is a mixture of an alcohol and water having a volume percent alcohol between about 5 vol-% and about 20 vol-%, as determined by known methods, for example gas chromatography. The concentration of product in the solution or suspension to be chromatographically treated is also varied according to the particular embodiment, but is generally between about 0.1 and about 10 g/L. Preferably, the concentration of the product to be treated is such that column loading is between about 1 g/L and 12 g/L.

The reverse phase liquid chromatography column can be conditioned by eluting the column with a conditioning volume of a conditioning liquid, preferably an aqueous solvent. The conditioning volume is preferably between about 1 and about 10 column volumes.

The product to be treated is loaded onto the conditioned stationary phase of the reverse phase chromatography column by means of a solution, a slurry, or, a loading concentrate obtained by evaporating an aqueous solvent, preferably alcohol, from a composition containing the product. Loading of the column is accomplished by eluting the solution, slurry, or loading concentrate through the column. Preferably, elution of the solution, slurry, or loading concentrate is followed by elution with a washing elution volume comprising an aqueous solvent having the same composition as the aqueous solvent of the solution, slurry, or loading concentrate used to load the column stationary phase. The washing elution volume, when one is used, is preferably between about I and about 10 column volumes.

A further embodiment of the present invention provides a third product from an MD-1 reverse phase liquid chromatography process having at least about 20% by weight and more preferably at least about 24% by weight of a mixture of trihydroxystilbenes and mono-β-D-glycosylated trihydroxystilbenes. In a preferred embodiment of the MD-I process, the first product of the present invention is slurried in an aqueous solvent, preferably a mixture comprising between about 3 vol-% and about 7 vol-% alcohol, preferably methanol. The first product is loaded onto an MD-1 column support by eluting the slurry through the MD-1 column and can be followed by a washing elution volume including an aqueous solvent that is preferably a mixture of alcohol and water having between about 5 vol-% and about 20 vol-% alcohol, preferably methanol. A composition including the third product can be eluted from the loaded MD-1 column stationary phase with a first MD-1 elution volume to produce a first MD-1 effluent. The first MD-1 elution volume includes an aqueous solvent, preferably a mixture of alcohol and water having between about 70 vol-% and about 80 vol-%, preferably about 75 vol-%, of an alcohol, preferably a methanol. Aqueous solvent can be removed from the first MD-1 effluent composition by any suitable means as discussed above, to obtain the third product.

Yet another embodiment of the present invention provides a fourth product having at least about 30% by weight of a stilbene fraction having a mixture of trihydroxystilbenes and mono-β-D glycosylated trihydroxystilbenes. The fourth product can be obtained by a first MD-2 reverse phase liquid chromatography process.

Starting material for a first MD-2 process is a first MD-2 loading concentrate having a third product of the present invention in an aqueous solvent, preferably a mixture of alcohol and water comprising not more than about 20 vol-% alcohol, preferably methanol. The MD-2 loading concentrate can be made by removing sufficient aqueous solvent from the first MD-1 effluent resulting from the first MD-1 elution volume so that the solids content of the first MD-2 loading concentrate is at least about 10 g/L, preferably at least about 13 g/L. The third product is loaded onto an MD-2 column stationary phase by eluting the first MD-2 loading concentrate through the MD-2 column which can be followed by a washing elution volume. The MD-2 column is then eluted with a first MD-2 elution volume to make a first MD-2 effluent. In one embodiment, the first MD-2 elution volume is a mixture of an alcohol, preferably methanol, and water having at least about 60 vol-% and preferably at least about 70 vol-% alcohol, more preferably at least about 75 vol-% alcohol.

In another embodiment, a second MD-2 process, which includes the steps of the first MD-2 process, the MD-2 column is eluted with a first MD-2 elution volume of a second MD-2 process that includes at least a first gradient volume and a second gradient volume, both of which are mixtures of an alcohol, preferably methanol and water, and both of, which can be divided into any number of subgradient volumes. In a preferred embodiment, the first gradient volume includes between about 20 vol-% and about 40 vol-%, preferably at least about 30 vol-%, of an alcohol, preferably methanol, and the second gradient volume includes between about 70 vol-% to about 80 vol-%, preferably at least about 75 vol-%, of an alcohol, preferably methanol.

In those embodiments of the second MD-2 process in which the first MD-2 elution volume of a second MD-2 process has first and second gradient volumes, the effluent that results from elution of the first and second gradient volumes can be fractionate collected and segregated into first and second gradient fractions, respectively, of the second MD-2 process that are compositions containing specific embodiments of the fourth product of the present invention. Furthermore, either gradient fraction can itself be fractionate collected to obtain gradient subfractions.

In preferred embodiments of the second MD-2 process in which the first gradient volume is a mixture of alcohol and water having about 30 vol-% methanol and the second gradient volume is a mixture of alcohol and water having about 70 vol-% methanol, the first gradient fraction is a composition including a fourth product of the present invention that includes at least about 40% by weight of a stilbene fraction that includes at least about 90% mono-β-D-glycosylated trihydroxystilbenes and the second gradient fraction is a composition also including a fourth product of the present invention including at least about 30% by weight of a stilbene fraction that has at least about 80% trihydroxystilbenes, preferably 3,4',5-trihydroxystilbenes.

The respective fourth products can be obtained by removing alcohol-water mixture from the respective gradient fractions.

Another embodiment of the present invention provides a third MD-2 process for making a composition that includes a stilbene fraction that has at least about 80% and preferably at least about 90% by weight mono-β-D-glycosylated-3,4', 5-trihydroxystilbene. In a third MD-2 process, a third product is loaded onto an MD-2 column stationary phase by means of an MD-2 loading concentrate. The MD-2 column is eluted with a first MD-2 elution volume of a third MD-2 process. In a preferred embodiment, the first MD-2 elution volume of a third MD-2 process is an MD-2 gradient elution volume including a mixture of alcohol and water the composition of which can be varied linearly, exponentially, logarithmically, parabolically, step-wise, or according to any combination of the foregoing. The MD-2 effluent is fractionate collected to obtain one or more compositions, each of which contains a fourth product.

Another embodiment of the present invention provides a fifth product that has at least about 60%, preferably at least about 65%, of a stilbene fraction containing at least about 90% by weight of mono-β-D-glycosylated-3,4',5-trihydroxy-trans-stilbene. This embodiment of the fifth product of the present invention can be made in a first MD-3 reverse phase chromatography process. Starting material for this first MD-3 reverse phase chromatography process is a loading concentrate made by removing sufficient aqueous solvent from the segregated first gradient fraction of the second MD-2 process or a segregated fraction of the third MD-2 process that includes a stilbene fraction that has at least about 50% of mono-β-D-glycosylated-3,4'5-trihydroxystilbenes, so that the loading concentrate has a solids content of at least about 3 g/L. In preferred embodiments in which the first gradient volume of the second MD-2 elution volume is a mixture of alcohol and water, the loading concentrate preferably has not more than about 5% alcohol. The loading concentrate is eluted through an MD-3 column to load the column stationary phase and, in preferred embodiments, is followed by a washing elution that is an aqueous solvent, preferably a mixture of alcohol and water having about 5 vol-% alcohol, preferably methanol, and the volume of the loading elution corresponds to about 0.5 to about 10 column volumes. The MD-3 column is then eluted with a first MD-3 elution volume of the first MD-3 process to obtain a first MD-3 effluent of a first MD-3 process that is fractionate collected to obtain a first fraction of a first MD-3 effluent of a first MD-3 process and a second fraction of a first MD-3 effluent of a first MD-3 process. In preferred embodiments the first fraction of the first MD-3 effluent of a first MD-3 process amounts to about 0.5 to about 3, preferably about 1.5, column volumes and the second fraction of the first MD-3 effluent of a first MD-3 process amounts to between about 0.5 and about 3 column volumes, preferably 1 column volume. The fifth product that has at least about 60% of a stilbene fraction comprising at least about 90% mono-β-D-glycosylated-3,4',5-trihydroxy-trans-stilbene can be obtained by removing the aqueous solvent from the fractionate collected first MD-3 effluent of a first MD-3 process.

In another embodiment, the present invention provides an evaporative crystallization process for making a fifth product containing at least about 85% and preferably at least about 90% by weight 3,4',5-trihydroxy-trans-stilbene-3-β-mono-D-glucoside. The starting point for the evaporative crystallization process is fractionate collected first MD-3 effluent of a first MD-3 process, preferably a second fraction of a first MD-3 effluent of a first MD-3 process that is fractionate collected after a first fraction of a first MD-3 effluent of a first MD-3 process amounting to 0.5 to about 3 column volumes is collected. The second fraction of a first MD-3 effluent of a first MD-3 process is evaporated to between about 0.1 and about 0.2 times its original volume and cooled, preferably to 4° C. or below, to form crystals that are a fifth product containing at least about 85% 3,4',5-trihydroxy-trans-stilbene-3-β-mono-D-glucoside.

In another embodiment, the present invention provides a sixth product having at least about 70% and preferably at least about 75% of a stilbene fraction including at least about 70% by weight of 3,4',5-trihydroxy-trans-stilbene. The sixth product can be prepared by a second MD-3 process. The starting material for the second MD-3 process is the second gradient fraction of the second MD-2 process. Aqueous solvent is removed from the second MD-2 gradient fraction of the second MD-2 process to form a loading concentrate having a solids content of at least about 7 g/L. The loading concentrate is eluted through an MD-3 column and, in preferred embodiments, can be followed by a washing elution volume including an aqueous solvent, preferably a mixture of alcohol and water including between about 10 vol-% and about 20 vol-% alcohol, preferably methanol. The MD-3 column is then eluted with a first MD-3 elution volume of a second MD-3 process having first and second gradient volumes. The first gradient volume of the first MD-3 elution volume of the second MD-3 process is preferably an aqueous solvent that is preferably a mixture of alcohol and water having between about 35 vol-% and about 45 vol-%, preferably 40 vol-%, of an alcohol, preferably methanol, and elutes a first MD-3 gradient fraction of a second MD-3 process and is followed by elution with the second MD-3 gradient volume of a first MD-3 elution volume of the second MD-3 process that includes an aqueous solvent, preferably an alcohol-water mixture having between about 50 vol-% and about 60 vol-%, preferably about 65 vol-%, of an alcohol, preferably methanol, to elute a second MD-3 gradient fraction of the second MD-3 process. The sixth product of the present invention can be obtained by removing the aqueous solvent from the second MD-3 gradient fraction of the second MD-3 process.

In other embodiments, the present invention provides a sixth product that includes at least about 85% and preferably at least about 90% trans-resveratrol (3,4',5-trihydroxy-trans-stilbene) which can be obtained by an extraction process. In one embodiment, the extraction process includes removing aqueous solvent from the second MD-3 gradient fraction of a second MD-3 process to attain a solids content of at least about 1.5 g/L and twice contacting the so concentrated second MD-3 gradient volume with one or more extraction volumes, each preferably 0.5 to 2 times the volume of the so concentrated second MD-3 gradient volume, of a polar organic solvent, preferably ethyl acetate. The extraction volumes are combined and the polar organic solvent is removed to obtain the sixth product having at least about 85% by weight trans-resveratrol.

Yet another embodiment of the present invention is a crystallization process for making the substantially colorless product which comprises removing the aqueous solvent from the second MD-3 gradient volume of a first MD-3 elution volume of a second MD-3 process, dissolving the resulting solid at T>10° C. in methanol, cooling to T<0° C. form crystals of the substantially colorless product and recovering the crystals of substantially colorless product by conventional means.

In another embodiment, the invention provides a partition crystallization process for making a sixth product that contains at least about 80% and preferably at least about 85% 3,4',5-trihydroxy-trans-stilbene. Starting point for the partition crystallization process is a second MD-3 gradient fraction of a second MD-3 process. The second MD-3 gradient fraction is concentrated under vacuum to 0.35 to 0.40 times its original volume and a solid concentration of at least about 1,5 g/L. The concentrated gradient fraction is contacted with a polar organic solvent, preferably ethyl acetate. Preferably, the volume of the polar organic solvent used is between bout 0.75 and about 0.85 time the volume of the concentrated second gradient fraction. In preferred embodiments, the gradient fraction is contacted serially with two separate volumes of polar organic solvent and the volumes are combined. The polar organic solvent, from single or multiple contactings, are evaporated to dryness to yield a sixth product having at least 80% 3,4',5-trihydroxy-trans-stilbene.

Yet another embodiment of the present invention provides a seventh product that has at least about 50% and preferably at least about 55% more preferably at least about 60%, by weight of a stilbene fraction that includes at least about 50% by weight of 3,4',5-trihydroxy-cis-stilbene.

The seventh product of the present invention can be prepared by a third MD-3 reverse phase liquid chromatography process. Starting material for the third MD-3 process is a second MD-2 gradient fraction of a second MD-2 process from which aqueous solvent is removed to form a loading concentrate having a solid content of at least 7 g/L. The loading concentrate thus formed is eluted through a conditioned MD-3 column. In preferred embodiments, elution of the loading concentrate can be followed by elution of a washing elution volume including an aqueous solvent, preferably a mixture of alcohol and water having between about 5 vol-% and about 20 vol-% alcohol, preferably methanol. The washing elution volume, when used, is followed by first and second MD-3 elution volumes of the third MD-3 process to produce, respectively, first and second effluents of the third MD-3 process. The first MD-3 elution volume of the third MD-3 process can include an aqueous solvent of a particular composition and can have two or more gradient volumes that when fractionate collected, result in two or more gradient fractions of a first effluent of the third MD-3 process. The first and second MD-3 elution volumes of the third MD-3 process include aqueous solvents which, in preferred embodiments, are mixtures of alcohol and water.

The first MD-3 elution volume of the third MD-3 process preferably includes a mixture of alcohol and water comprising up to about 70% alcohol, preferably methanol. In one embodiment, the first MD-3 elution volume of the third MD-3 process comprises first and second gradient volumes of a first MD-3 elution volume of a third MD-3 process that are mixtures of alcohol, preferably methanol, and water wherein the first MD-3 gradient volume of a first MD-3 elution volume of a third MD-3 process has between about 35 vol-% and about 45 vol-%, preferably about 40 vol-%, alcohol and the second gradient volume of a first MD-3 elution volume of a third MD-3 process comprises between about 50 vol-% and about 60 vol-%, preferably about 55 vol-%, alcohol. In other embodiments, the first elution volume of the third MD-3 process is a gradient elution volume and includes an aqueous solvent the composition of which is varied over the course elution of the first elution volume of a third MD-3 process according to a predetermined program. The program may be linear, exponential, logarithmic, hyperbolic, step-wise, or a combination of the foregoing. For example, if the aqueous solvent is a mixture of alcohol and water, the volume percent alcohol can be varied from about 20 vol-% to about 60 vol-% during elution of the first MD-3 elution volume of the third MD-3 process.

The volume of this first MD-3 elution volume of the third MD-3 process is from about 1 to about 12 column volumes, preferably less than about 8 column volumes.

The second elution volume of the third MD-3 process is preferably a mixture of an alcohol, preferably methanol, and water including between about 80 vol-% and about 90 vol-%, preferably about 75 vol-% of alcohol. The seventh product can be obtained by collecting a second MD-3 effluent of a third MD-3 process eluted by the second MD-3 elution volume of the third MD-3 process and removing the aqueous solvent therefrom.

The second MD-3 effluent of a third MD-3 process eluted by the second MD-3 elution volume of a third MD-3 process can be fractionate collected. When the second MD-3 effluent of a third MD-3 process is fractionate collected, it may be collected in any number of fractions. In a preferred embodiment, the second effluent of the third MD-3 process is fractionate collected in two fractions. The first fraction of the second effluent of the third MD-3 process preferably amounts to between about 0.5 and about 1 column volume. The second fraction of the second effluent of the third MD-3 process preferably amounts to between about 0.5 and 2.0 column volumes and is a composition including the seventh product of the present invention.

In the following examples, "% alcohol" indicates the volume percent (vol-%) of alcohol in an alcohol—water mixture. Analysis of stilbene fractions was performed used HPLC on a Hewlett Packard Series 1100 HPLC using an ODS Hypersil column.

EXAMPLE 1

This example illustrates an MD-1 process.

The dried ground roots of Huzhang (*Polygonum cuspidatum*) was extracted three times by percolation with 75% ethanol. The ethanol extract was concentrated at reduced pressure to a brown gummy semisolid (called Native Extract and abbreviated NE). The temperature during evaporation was kept between 35° C. and 40 and the pressure was kept between 15~25 mm. About 1.4 kg of the NE (wet solid, Lot No. 7-1752) were dissolved in 4.9 L MeOH at 45° C. and were stirred for 30 min. 44.1 L H$_2$O were added to the mixture (to yield 10% MeOH). The resulting mixture was loaded onto a water-conditioned, 4 in.×35 in. MD-1 column (containing Amberlite® resin, XAD-16HP). The column was eluted with a washing elution volume (2 CV of 10% MeOH) and then eluted with a first MD-1 elution volume (7.7 CV of 75% MeOH) to obtain a first MD-1 effluent. The first MD-1 effluent (the best pool of fractions) from the MD-1 column was concentrated from 126.4 L (75% MeOH ) to 35.5 L (19.5% MeOH) at 45° C. for 1.5 hrs under vacuum in a still to form an MD-2 loading concentrate. Analysis indicated that the solids recovery is quantitative and the stilibene fraction of the solid component of the first MD-1 effluent amounts to 24.2%.

EXAMPLE 2

This example illustrates a second MD-2 process.

The MD-2 loading concentrate from Example 1 was loaded onto a 10% MeOH conditioned, 4"×49" MD-2 column having a polyamide resin as the stationary phase. The column was gradient eluted with a first gradient volume of a first MD-2 elution volume of a second MD-2 process (8 CV of 35% MeOH) and a second gradient volume of a first MD-2 elution volume of a second MD-2 process (6 CV of 75% MeOH). The first and second gradient fractions from 35% MeOH and 75% MeOH gradient volumes were fractionate collected.

The solids component of first gradient fraction had a stilbene fraction of 44.4%, of which 60% was mono-β-D-glycosylated trihydroxy-trans-stilbene. The solids component of the second gradient fraction had a stilbene fraction of 35% of which 86% was trihysroxtstilbenes.

EXAMPLE 3

This example illustrates removal of aqueous solvent from a composition.

The alcohol—water mixture was removed from the second gradient fraction of Example 2 using a rotary evaporator (Büichi Rotavapor Model R-187) followed by drying in an tray vacuum oven. About 2 L of the second gradient fraction (BZ1-57-3 resveratrol pool, 75% MeOH, 35.% total stilbene, 86% thereof trans-resveratrol and cis-resveratrol) were rotary evaporated to 555 ml (approx. 10% MeOH) at 32° C. and 70~110 psi for 7 hours. About 30 ml of the resulting solution was transferred onto a metal dish and dried in a vacuum oven at 42° C., 30" water vacuum for 15 hours. About 281.4 mg of dried fourth (resveratrol) product were obtained.

EXAMPLE 4

This example illustrates making a sixth product of the present invention by a second MD-3 process.

20 L of a second MD-2 gradient fraction from a second MD-2 process (BZ1-57-3: 16.1% trans-resveratrol, 8.4 g; 13.9% cis-resveratrol, 7.2 g; 1.4% trans-piceid, 0.7 g; 3.6% cis-piceid, 1.8 g; total stilbene, 18.2 g; 75% MeOH) were rotary evaporated to form an MD-3 loading concentrate (6.28 L, approx. 20% MeOH) that was eluted through a conditioned (20% MeOH) 4"×52" MD-3 column (C18 bonded silica gel) to load the stationary phase of the column. The column was gradient eluted with 3.7 CV of a first MD-3 elution volume of a second MD-3 process (40% MeOH) followed by 1.5 CV of a second MD-3 elution volume of a second MD-3 process (55% MeOH) that resulted in 1.5 CV of a second MD-3 effluent of a second MD-3 process. The best pool of trans-resveratrol was fractionate collected as the first 1.1 CV of the second MD-3 effluent of a second MD-3 process, which contained a sixth product having a stilbene fraction that was 74.7% trihydroxy-trans-stilbene. Thus, 86.2% of the trihydroxy-trans-stilbenes present in the second gradient volume of the second MD-2 process were recovered.

EXAMPLE 5

This example illustrates a partition crystallization process for purification of trihydroxy-trans-stilbene.

About 15 L of the above second MD-3 effluent of the second MD-3 process of Example 4 (resveratrol best pool BZ1-60-13~17, 75% MeOH-water, 9.723 g 74.7% trihydroxy-trans-stilbene) were rotary evaporated to a volume of 5.7 L (approx. 33% MeOH). The solution was twice extracted with 0.79 times its volume of ethyl acetate. Ethyl acetate layers from each extraction were then combined and evaporated to dryness. About 7.8 g of dry solids containing 6.7 g 82% trihydroxy-trans-stilbene (trans-resveratrol) were obtained. The solids were crystallized in 40 ml of methanol at −10° C. About 5.8 g of colorless crystal (90% purity, 81.1% recovery) were obtained.

EXAMPLE 6

This example illustrates making a fifth product by a first MD-3 process.

About 37 L (75 g solid) of a first gradient subfraction of a first gradient fraction of a second MD-2 process (BZ1-57-1:34. 15% trans-resveratrol, 22 g; 0.49% cis-resveratrol, 0.31 g; 0.25% trans-piceid, 0.16 g; 4.54% cis-piceid, 2.9 g; 39.4% total stilbene, 29.4 g; in 35% MeOH) was rotary evaporated to 24.7 L (5% MeOH) and was loaded onto a $H_2O$ conditioned 4"×52" MD-3 column (C-18 bonded silica gel). The column was eluted with a first MD-3 elution volume of a first MD-3 process (3.6 CV of 30% MeOH). The resulting first MD-3 effluent of a first MD-3 process was fractionate collected. The best pool of trans-piceid was fractionate collected between 1.68 CV and 2.20 CV (total of 0.52 CV) of the first MD-3 effluent of a first MD-3 process. The content of trans-piceid in the stilbene fraction of the solid component of the best pool was 66% and 94% of the trans-piceid loaded onto the MD-3 column was recovered.

EXAMPLE 7

This Example illustrates evaporative crystallization to increase the purity of trans-piceid.

About 9 L of above best pool of trans-piceid fractions fractionate collected from the first MD-3 effluent of the first MD-3 process of Example 7 (BZ1-64-6~8, 30% MeOH, 31.47 g of 65.7% trans-piceid) were concentrated (rotary evaporation) to 1.3 L, chilled and crystallized at 4° C. (73 ml cold $H_2O$/g crystal), and filtered with #5 Whatman paper. The peach-colored crude crystal was washed with 100 ml of cold $H_2O$ three times to remove the color completely. This procedure yielded 18 g of colorless trans-piceid crystals of 90% purity; with 80% recovery of the trans-piceid loaded onto the MD-3 column.

EXAMPLE 8

The following Example illustrates making the third product by an MD-1 process.

About 1.5 kg (wet wt, 0.95 kg dry wt.) of NE (Lot # 7-1752, 5.9% trans-piceid, 0.96% cis-piceid, 2.1% trans-resveratrol, 2.9% cis-resveratrol, 11.9% total stilbene) was dissolved in 3.5 L of SDA (95% EtOH) and made up to 35 L with $H_2O$ to make a 10% SDA solution. The solution was loaded onto a 15×99 cm MD-1 column (Amberlite® polystyrenic resin, XAD- 16HP, 17.5 L per column volume). Prior to use, the column was conditioned with 1 CV of 10% SDA at 7.2 g stilbene/L resin. The column was eluted with a washing elution volume (1 CV of 10% SDA) and then eluted with a first MD-1 elution volume (3 CV of 90% SDA) to produce a first MD-1 effluent. The first MD-1 effluent was fractionate collected (½ CV per fraction) and the later 2½ CV (CK2-25-3~4) were pooled and collected as a composition containing the third product. The solids component of the combined later 2½ fractionate collected pool amounted to 424.2 g having a 25.5% stilbene fraction.

EXAMPLE 9

The following example illustrates a first MD-2 process for making a fourth product having 40% of a stilbene fraction.

About 44.4 L of 90% SDA containing a third product from a MD-1 process (319 g solid, 27% total stilbene, 13% trans-piceid, 2.3% cis-piceid, 4.7% trans-resveratrol, 5.6% cis-resveratrol) was evaporated to 9.6 L of 35% SDA, using a Büchi Rotavapor R-187, to form a first MD-2 loading concentrate. About 7 L of the first MD-2 loading concentrate were diluted to 9.8 L with $H_2O$ to bring the SDA content to 25 vol-%. The diluted loading concentrate was loaded onto a 10×117 cm water-conditioned MD-2 column (polyamide, 9.6 L/CV). The loading was 8.9 g stilbene/L of stationary phase. The column was eluted with a washing elution volume (4 CV of 20% SDA) and was eluted with a first MD-2 elution volume of a first MD-2 process (4 CV of 75% SDA) to make a first MD-2 effluent.

SDA-water mixture was removed from the first MD-2 effluent. 195 g of solid third product having a 40% stilbene fraction were obtained (22% trans-piceid, 2.4% cis-piceid, 5.7% trans-resveratrol, 9.4% cis-resveratrol). Approximately 90% of the stilbenes in the loading concentrate were recovered.

EXAMPLE 10

2 g NE (first product from Polygonum cuspidatum, lot # 7-1752, 5.9% trans-piceid, 1% cis-piceid, 2.1% trans-resveratrol, 2.9% cis-resveratrol, 11.9% total stilbene) were mixed with 5 ml of concentrated hydrochloric acid and 95 ml of DI-water (5% HCl). The solution was refluxed with agitation at 80° C. under nitrogen for 60 minutes. trans-Resveratrol (0.13 g) was isolated from the solution. Thus, 81.3% of all trihydroxystilbenes were converted to trans-resveratrol (trans-3,4',5-trihydroxystilbene).

EXAMPLE 11

The following example illustrates conversion of a β-D-glycosylated stilbene to the aglycone. 200 mg of 90% trans-piceid (3,4'5-trans-trihydroxystilbene -3-β-mono-D-glucoside, BZ1-69-1) was mixed with 5 ml of concentrated hydrochloric acid and 95 ml water (5% HCl v/v) and refluxed with agitation at 100° C. for 90 minutes to yield 114 g (57% yield) trans-resveratrol (trans-3,4',5-trihydroxystilbene).

EXAMPLE 12

The following example describes an In vivo study that showed that the levels of DNA-synthesis in HL-60 cells were 87%, 89%, and 79% inhibited, respectively, when cells are treated with 80 µg/ml concentrations of mixtures containing third products having 30% resveratrol, 40% stilbene, and 40% piceid, respectively. RNA synthesis levels were also inhibited by the aforementioned compounds at a concentration of 80 µg/ml by 93%, 91%, and 81%, respectively. The amount of 3[$H_2O$] released as a byproduct of DMBA metabolism was inhibited by percentages of 69%, 70%, and 58% of the three previously mentioned compounds respectively, also at a concentration of 80 μg/ml. Test results are given in the Tables below.

TABLE 1

Inhibitory Effect of a Third Product (30% Resveratrol) on the Synthesis of DNA in HL-60 Cells.

| Composition Containing 3rd Product (30%-Resveratrol) (μg) | [$^3$H] Thymidine Incorporation into DNA (cpm) | Percent Inhibition |
|---|---|---|
| 0 | 32880 ± 432 | — |
| 2.5 | 23166 ± 3178 | 30 |
| 5.0 | 14575 ± 1165 | 56 |
| 10.0 | 10856 ± 1004 | 67 |
| 20.0 | 6307 ± 828 | 81 |
| 40.0 | 5762 ± 652 | 83 |
| 80.0 | 4328 ± 337 | 87 |

The third product used in this experiment was obtained from the second gradient faction of a second MD-2 process according to the method of Example 2. HL-60 ($5 \times 10^5$ cells) in 1 ml RPMI medium were incubated with various concentration of 30% resveratrol at 37° C. in a 5% $CO_2$ atmosphere incubator for 90 minutes. [$^3$H] thymidine incorporation into DNA was determined.

TABLE 2

Inhibitory Effect of a Third Product (40% Piceid) on the Synthesis of DNA in HL-60 Cells.

| Composition Containing 3rd Product (40% Piceid) (μg) | [$^3$H] Thymidine Incorporation into DNA (cpm) | Percent Inhibition |
|---|---|---|
| 0 | 32880 ± 432 | — |
| 2.5 | 22733 ± 864 | 31 |
| 5.0 | 21266 ± 206 | 35 |
| 10.0 | 19740 ± 1234 | 40 |
| 20.0 | 16507 ± 864 | 50 |

TABLE 2-continued

Inhibitory Effect of a Third Product (40% Piceid) on the Synthesis of DNA in HL-60 Cells.

| Composition Containing 3rd Product (40% Piceid) (μg) | [$^3$H] Thymidine Incorporation into DNA (cpm) | Percent Inhibition |
|---|---|---|
| 40.0 | 10704 ± 1058 | 67 |
| 80.0 | 7194 ± 746 | 78 |

The third product used in this Example was obtained from the first gradient fraction of a second MD-2 process according to the method of Example 2. HL-60 ($5 \times 10^5$ cells) in 1 ml RPMI medium were incubated with various Concentration of 30% resveratrol at 37° C. in a 5% $CO_2$ atmosphere incubator for 90 minutes. [$^3$H] thymidine incorporation into DNA was determined.

TABLE 3

Inhibitory Effect of a Third Product (40% Stilbene) on the Synthesis of DNA in HL-60 Cells.

| Composition Containing Third Product (40% Stilbene Fraction) (μg) | [$^3$H] Thymidine Incorporation into DNA (cpm) | Percent Inhibition |
|---|---|---|
| 0 | 32880 ± 432 | — |
| 2.5 | 18123 ± 2037 | 45 |
| 5.0 | 15483 ± 631 | 53 |
| 10.0 | 14410 ± 144 | 56 |
| 20.0 | 7888 ± 86 | 76 |
| 40.0 | 5388 ± 360 | 84 |
| 80.0 | 3775 ± 137 | 89 |

The third product used in this Example was obtained from the first elution volume of a first MD-2 process. HL-60 ($5 \times 10^5$ cells) in 1 ml RPMI medium was incubated with various concentration of 30% resveratrol at 37° C. in a 5% $CO_2$ atmosphere incubator for 90 minutes. [$^3$H] thymidine incorporation into DNA was determined.

TABLE 4

Effect of A second Product (8% Stilbene Fraction) and Sulforpbane on DMBA-induced Mammary Carcinogenesis in Rats.

| | Treatment | | | | | | | |
|---|---|---|---|---|---|---|---|---|
| | Control Diet + Corn Oil | | Control Diet + DMBA | | Sulforaphane + CMBA | | Second Product + DMBA | |
| | Number of Rats Per Group | | | | | | | |
| | 7 | | 26 | | 16 | | 20 | |
| Weeks After DMBA | Tumors Per Rat | Rat with Tumors (%) | Tumors Per Rat | Rat with Tumors (%) | Tumors Per Rat | Rat with Tumors (%) | Tumors Per Rat | Rat with Tumors (%) |
| 9 | 0 | 0 | 0.12 ± 0.06 | 12 | 0 (100%) | 0 (100%) | 0 (100%) | 0 (100%) |
| 14 | 0 | 0 | 0.23 ± 0.10 | 19 | 0.13 ± 0.08 (43%) | 13 (32%) | 0.15 ± 0.11 (38%) | 10 (47%) |
| 22 | 0 | 0 | 0.77 ± 0.21 | 50 | 0.36 ± 0.33 (10%) | 31 (38%) | 0.50 ± 0.22 (35%) | 30 (40%) |

Female Sprague-Dawley rats were given AIN 76A diet or AIN 76A diet containing 1% of a second product (approximately 0.08% resveratrol) at 2 weeks before oral administration of 7,12-dimethylbenz[a]anthracene (DMBA), and continuing until the end of the experiment. Sulforaphane was orally administered by gavage (50 mg/kg body weight in 0.1 ml corn oil) to rats once a day at 46[th], $47^{th}$, $48^{th}$, $49^{th}$, $50^{th}$ and $51^{st}$ days of their age. DMBA (8 mg/rat) in 1 ml corn oil was intubated to rats at 50 days old. Palpable mammary tumors were counted every week after DMBA administration.

EXAMPLE 14

The following Example illustrates the anti-tumor properties against various human tumor cell lines exhibited by various products of the present invention according to the results of in vitro 6-cell line clinical test.

The tests were performed according to the MTT assay (See, Mosmann, T., *J. Immun. Meth.*, 65, 55(1983).

Cells were planted in 96 well flat bottom plates with low evaporation lids. Three cell lines per plate were seeded in 0.2 ml medium per well. Each cell line was planted at the optimum concentration for its particular growth rate: H-29 and A-549, 5000 c/ml, MCF-7, 15000 c/well, KB and similar cells, 2500 c/ml, P388 and similar cells, 15000 c/ml. Products were tested at various dilutions (at least ten) to determine the ED 50.

water having at least about 70%-vol % alcohol to isolate a fourth product comprising at least 30% by weight of a stilbene fraction, wherein the stilbene fraction comprises about 80% by weight trihydroxystilbenes;

(h) loading a loading concentrate of the fourth product onto an MD-3 column with a stationary phase selected from the group consisting of C-8 to C-18 and cyano bonded silica gel;

(i) eluting the MD-3 column with a first gradient volume comprising a mixture of alcohol and water between about 35 and 45 vol-% alcohol;

(j) eluting the MD-3 column with a second gradient volume comprising a mixture of alcohol and water between about 50 and 60 vol-% alcohol to isolate a sixth product comprising at least about 70% of a stilbene fraction, wherein the stilbene fraction comprises at least about 75% by weight of 3,4',5-trihydroxy-trans-stilbene; and (k) crystallizing the purified product from the sixth product.

TABLE 5

6-Cell Line Clinical Test Results.

| Sample Description | Lot# | Kidney A-478 ED 50 ($\mu$g/ml) | Prostrate PC-3 ED 50 ($\mu$g/ml) | Pancreatic PACA-2 ED 50 ($\mu$g/ml) | Lung A-549 ED 50 ($\mu$g/ml) | Breast MCF-7 ED 50 ($\mu$g/ml) | Colon HT-29 ED 50 ($\mu$g/ml) |
|---|---|---|---|---|---|---|---|
| Second Product, 8% Stilbene Fraction | 7-1752 | 276.61 | 14.42 | 45.32 | 77.86 | 521.37 | 41.65 |
| Fifth Product, 90% Piceid | BZ1-069-1 | 34.95 | 80.58 | 40.98 | 35.77 | 100 | 79.20 |
| Sixth Product, Recryst., 90%, Resveratrol | BZ1-67-2 | $7.40 \times 10^{-1}$ | 100 | 3.55 | $3.26 \times 10^{-1}$ | 4.23 | 1.66 |
| Fourth Product, First MD-2 Process, 40%, Stilbene Fraction | CK1-100-3 | 19.57 | 100.00 | 7.18 | 3.55 | 77.96 | 18.01 |
| Doxorubicin HCL (Control) | | $3.59 \times 10^{-3}$ | $2.81 \times 10^{-2}$ | $5.22 \times 10^{-3}$ | $3.16 \times 10^{-3}$ | $1.07 \times 10^{-1}$ | $2.20 \times 10^{-2}$ |

We claim:

1. A process for the isolation of a purified product comprising at least about 85% by weight of 3,4',5-trihydroxy-trans-stilbene from a plant material containing trihydroxystilbenes and glycosylated derivatives thereof, the process comprising:
   (a) contacting pieces of the plant material with an aqueous solvent to form a slurry;
   (b) separating the contacted aqueous solvent from the slurry to isolate a first product comprising at least 10% by weight of a mixture of trihydroxystilbenes and mono-β-D-glycosylated trihydroxystilbenes;
   (c) loading a loading concentrate of the first product onto an MD-1 column with a stationary phase comprising a copolymer of a vinyl aromatic compound cross-linked with a polyvinyl aromatic compound;
   (d) eluting the MD-1 column with an elution volume comprising a mixture of alcohol and water between about 70 and 80 vol-% alcohol to isolate a third product comprising at least 20% by weight of a mixture of trihydroxystilbenes and mono-β-D-glycosylated trihydroxystilbenes;
   (e) loading a loading concentrate of the third product onto an MD-2 column with a stationary phase comprising polyamide resin;
   (f) eluting the MD-2 column with a first MD-2 gradient volume comprising a mixture of alcohol and water between about 20 and 40-vol % alcohol;
   (g) eluting the MD-2 column with a second MD-2 gradient volume comprising a mixture of alcohol and 2. The process of claim 1, wherein the plant material is *Vitis vinefera*.

3. The process of claim 1, wherein the plant material is *Polygonum cuspidatum*.

4. The process of claim 1, wherein the aqueous solvent of (i) comprises 75 vol-% SDA.

5. The process of claim 1, wherein the alcohol is methanol.

6. The process of claim 1, wherein the alcohol is ethanol.

7. The process of claim 1, wherein the stationary phase of the MD-1 column of (c) is a copolymer of styrene and divinyl benzene.

8. The process of claim 1, wherein the stationary phase of the MD-2 column of (e) is selected from the group consisting of poly(caprolactam) and poly(hexamethylene adipamide).

9. The process of claim 1, wherein the stationary phase of the MD-3 column of (h) is C-18 bonded silica gel.

10. A process for the isolation of a purified product comprising at least 85% by weight mono-β-D-glycosylated 3,4',5-trihydroxy-trans-stilbene from a plant material containing trihydroxystilbenes and glycosylated derivatives thereof, the process comprising:
   (a) contacting pieces of the plant material with an aqueous solvent to form a slurry;
   (b) separating the contacted aqueous solvent from the slurry to isolate a first product comprising at least 10% by weight of a mixture of trihydroxystilbenes and mono-β-D-glycosylated trihydroxystilbenes;
   (c) loading a loading concentrate of the first product onto an MD-1 column with a stationary phase comprising a copolymer of a vinyl aromatic compound cross-linked with a polyvinyl aromatic compound;

(d) eluting the MD-1 column with an elution volume comprising a mixture of alcohol and water between about 70 and about 80 vol-% alcohol to isolate a third product comprising at least 20% by weight of a mixture of trihydroxystilbenes and mono-β-D-glycosylated trihydroxystilbenes;

(e) loading a loading concentrate of the third product onto an MD-2 column with a stationary phase comprising polyamide resin;

(f) eluting the MD-2 column with an elution volume comprising a mixture of alcohol and water between about 20 and 40 vol-% alcohol to isolate a fourth product comprising at least 50% by weight of a stilbene fraction comprising about 50% mono-β-D-glycosylated trihydroxystilbenes;

(g) loading a loading concentrate of the fourth product onto an MD-3 column with a stationary phase selected from the group consisting of C-8 to C-18 and cyano bonded silica gel;

(h) eluting the MD-3 column with an elution volume comprising a mixture of alcohol and water to isolate a fifth product comprising at least about 60% by weight of a stilbene fraction, wherein the stilbene fraction comprises at least about 90% by weight mono-β-D-glycosylated 3,4',5-trihydroxy-trans-stilbene; and (i) crystallizing the purified product from the fifth product.

11. The process of claim 10, wherein the plant material is *Vitis vinefera*.

12. The process of claim 10, wherein the plant material is *Polygonum cuspidatum*.

13. The process of claim 10, wherein the aqueous solvent of (a) comprises 75 vol-% SDA.

14. The process of claim 10, wherein the alcohol is methanol.

15. The process of claim 10, wherein the alcohol is ethanol.

16. The process of claim 10, wherein the stationary phase of the MD-1 column of (c) is a copolymer of styrene and divinyl benzene.

17. The process of claim 10, wherein the stationary phase of the MD-2 column of (e) is selected from the group consisting of poly(caprolactam) and poly(hexamethylene adipamide).

18. The process of claim 10, wherein the stationary phase of the MD-3 column of (g) is C-18 bonded silica gel.

* * * * *